(12) United States Patent
Harari et al.

(10) Patent No.: US 12,727,916 B2
(45) Date of Patent: Sep. 8, 2026

(54) FAILURE DETECTION AND SENSOR BASED CONTROL IN A MOTORIZED BONE FIXATION DEVICE

(71) Applicant: Synthes GmbH, Oberdorf (CH)

(72) Inventors: Shahar Harari, Tel-Aviv (IL); Oren Cohen, Moreshet (IL); Scott P. Lavoritano, West Chester, PA (US); Albert A. Montello, West Chester, PA (US)

(73) Assignee: Synthes GmbH, Oberdorf (CH)

( * ) Notice: Subject to any disclaimer, the term of this patent is extended or adjusted under 35 U.S.C. 154(b) by 0 days.

(21) Appl. No.: 18/754,812

(22) Filed: Jun. 26, 2024

(65) Prior Publication Data

US 2025/0000549 A1 Jan. 2, 2025

Related U.S. Application Data

(60) Provisional application No. 63/524,115, filed on Jun. 29, 2023.

(51) Int. Cl.

*A61B 17/62* (2006.01)
*A61B 5/00* (2006.01)

(Continued)

(52) U.S. Cl.

CPC ............ *A61B 17/62* (2013.01); *A61B 17/645* (2013.01); *A61B 90/06* (2016.02); *A61B 5/6811* (2013.01);

(Continued)

(58) Field of Classification Search

CPC ....... A61B 17/62; A61B 17/645; A61B 17/66; A61B 17/663; A61B 17/60; A61B 17/58;

(Continued)

(56) References Cited

U.S. PATENT DOCUMENTS

| | | | |
|---|---|---|---|
| 4,889,111 | A | 12/1989 | Ben-dov |
| 4,947,835 | A | 8/1990 | Hepburn et al. |

(Continued)

FOREIGN PATENT DOCUMENTS

| | | | |
|---|---|---|---|
| AU | 2013382253 | B2 | 11/2019 |
| AU | 2020354546 | A1 | 3/2022 |

(Continued)

OTHER PUBLICATIONS

Seide, K., et al., "Medical Robotics and Computer Assisted Surgery", 2004, pp. 64-69.

(Continued)

*Primary Examiner* — Marcela I. Shirsat
(74) *Attorney, Agent, or Firm* — Flaster Greenberg P.C.

(57) ABSTRACT

A control system for use with an adjustable bone fixation device having a frame connectible to bone tissue and a plurality of struts connected to the frame, the control system comprising: a plurality of actuators associated with the plurality of struts, each actuator configured for adjusting a length of at least one strut; and circuitry configured to: signal the plurality of actuators to adjust the struts according to a predefined actuation plan which sets operational parameters and permitted ranges thereof; determine a situation of potential failure associated with at least one actuator and involving at least one of the operational parameters being out of the permitted range; and implement, by signaling the at least one actuator, a recovery protocol designed to attempt completion of strut adjustment according to the predefined actuation plan.

12 Claims, 10 Drawing Sheets

(51) Int. Cl.

| | |
|---|---|
| *A61B 17/00* | (2006.01) |
| *A61B 17/17* | (2006.01) |
| *A61B 17/56* | (2006.01) |
| *A61B 17/58* | (2006.01) |
| *A61B 17/60* | (2006.01) |
| *A61B 17/64* | (2006.01) |
| *A61B 17/66* | (2006.01) |
| *A61B 17/88* | (2006.01) |
| *A61B 34/00* | (2016.01) |
| *A61B 34/10* | (2016.01) |
| *A61B 34/20* | (2016.01) |
| *A61B 34/30* | (2016.01) |
| *A61B 34/32* | (2016.01) |
| *A61B 90/00* | (2016.01) |

(52) U.S. Cl.

CPC ............... *A61B 2017/00017* (2013.01); *A61B 2017/00022* (2013.01); *A61B 2017/00075* (2013.01); *A61B 2017/00115* (2013.01); *A61B 2017/00119* (2013.01); *A61B 2017/00123* (2013.01); *A61B 2017/00132* (2013.01); *A61B 2017/00398* (2013.01); *A61B 17/171* (2013.01); *A61B 2017/564* (2013.01); *A61B 17/58* (2013.01); *A61B 17/60* (2013.01); *A61B 17/64* (2013.01); *A61B 17/6425* (2013.01); *A61B 17/6466* (2013.01); *A61B 17/66* (2013.01); *A61B 17/88* (2013.01); *A61B 34/10* (2016.02); *A61B 34/20* (2016.02); *A61B 34/25* (2016.02); *A61B 34/30* (2016.02); *A61B 34/32* (2016.02); *A61B 2090/061* (2016.02); *A61B 2090/065* (2016.02); *A61B 2090/066* (2016.02); *A61B 2562/0219* (2013.01); *A61B 2562/0247* (2013.01)

(58) Field of Classification Search

CPC . A61B 17/64; A61B 17/6425; A61B 17/6411; A61B 17/6466; A61B 17/171; A61B 17/88; A61B 2017/00017; A61B 2017/00119; A61B 2017/00398; A61B 2017/00084; A61B 2017/564; A61B 2017/00022; A61B 2017/00075; A61B 2017/00132; A61B 2017/00115; A61B 2017/00123; A61B 34/30; A61B 34/10; A61B 34/20; A61B 34/25; A61B 34/32; A61B 90/66; A61B 2090/061; A61B 2090/065; A61B 2090/066; A61B 2562/0219; A61B 2562/0247; A61B 5/6812; A61B 5/6811; A61B 2034/104

USPC ............................ 606/56, 53, 54, 57, 58, 59

See application file for complete search history.

(56) References Cited

U.S. PATENT DOCUMENTS 4,973,331 A 11/1990 Pursley et al.
5,108,394 A 4/1992 Kurokawa et al.
5,156,605 A 10/1992 Pursley et al.
5,180,380 A 1/1993 Pursley et al.
5,339,533 A 8/1994 Richardson
5,358,504 A 10/1994 Paley et al.
5,437,668 A 8/1995 Aronson et al.
5,728,095 A 3/1998 Taylor et al.
5,766,173 A 6/1998 Ross et al.
7,306,601 B2 12/2007 McGrath et al.
8,157,800 B2 4/2012 Vvedensky et al.
8,202,273 B2 6/2012 Karidis
8,282,652 B2 10/2012 Mackenzi et al.
8,333,766 B2 12/2012 Edelhauser et al.
8,491,660 B2 7/2013 Kaiser et al.
8,515,538 B1 8/2013 Osorio et al.
8,574,232 B1 11/2013 Ross et al.
8,585,703 B2 11/2013 Verma et al.
8,702,705 B2 4/2014 Ziran et al.
8,864,750 B2 10/2014 Ross et al.
8,864,763 B2 10/2014 Murray et al.
8,915,915 B2 12/2014 Harrison et al.
9,155,559 B2 10/2015 Ross et al.
9,186,180 B2 11/2015 Chang et al.
9,204,937 B2 12/2015 Edelhauser et al.
9,289,238 B2 3/2016 Ross et al.
9,524,581 B2 12/2016 Haskell
9,526,523 B2 12/2016 Aoki et al.
9,610,102 B2 4/2017 Singh
9,681,892 B2 6/2017 Ross et al.
9,717,528 B2 8/2017 Singh
9,788,861 B2 10/2017 Murray et al.
9,895,502 B2 2/2018 Hatanaka
9,918,742 B2 3/2018 Wilhelm et al.
9,949,758 B2 4/2018 Vikinsky et al.
10,010,350 B2 7/2018 Mannanal et al.
10,064,664 B2 9/2018 Forsell
10,080,586 B2 9/2018 Ross et al.
10,082,384 B1 9/2018 Singh
10,154,884 B2 12/2018 Kumar et al.
10,194,944 B2 2/2019 Edelhauser et al.
10,390,859 B2 8/2019 Sakkers et al.
10,492,832 B2 12/2019 Singh
10,631,897 B2 4/2020 Park et al.
10,881,433 B2 1/2021 Edelhauser et al.
10,898,229 B2 1/2021 Park et al.
10,932,713 B2 3/2021 Lewis et al.
10,945,765 B2 3/2021 Miller
10,962,166 B1 3/2021 Liu
11,076,801 B2 8/2021 Cohen et al.
11,083,497 B2 8/2021 Mannanal et al.
11,206,981 B2 12/2021 Chin
11,207,103 B2 12/2021 Singh
11,259,874 B1 3/2022 Landon et al.
11,266,444 B2 3/2022 Chen
11,304,757 B2 4/2022 Gutmann et al.
11,376,054 B2 7/2022 Kemper et al.
11,395,679 B2 7/2022 Noblett et al.
11,439,436 B2 9/2022 Gutmann et al.
11,471,192 B2 10/2022 Mullaney
11,600,368 B2 3/2023 Austin et al.
12,220,250 B2 2/2025 Cohen et al.
2002/0010465 A1 1/2002 Koo et al.
2006/0052782 A1 3/2006 Morgan et al.
2006/0276786 A1 12/2006 Brinker
2007/0043310 A1 2/2007 Trandafir et al.
2007/0055233 A1 3/2007 Brinker
2007/0150026 A1 6/2007 Bourget et al.
2007/0276786 A1 11/2007 Piedmonte
2008/0051779 A1 2/2008 Mackenzie et al.
2008/0139978 A1 6/2008 Talish et al.
2008/0234554 A1 9/2008 Vvedensky et al.
2010/0010576 A1 1/2010 Skelton et al.
2010/0087819 A1 4/2010 Mullaney
2011/0004199 A1 1/2011 Ross et al.
2013/0041288 A1 2/2013 Taylor et al.
2013/0131675 A1 5/2013 Vasta et al.
2013/0245625 A1 9/2013 Vasta et al.
2015/0164171 A1 6/2015 Margetis et al.
2016/0374561 A1 12/2016 Buescher et al.
2017/0071632 A1 3/2017 Vikinsky et al.
2017/0181800 A1 6/2017 Nikonovas
2019/0029727 A1 1/2019 Park et al.
2019/0277373 A1 9/2019 Matsuto et al.
2019/0282276 A1 9/2019 Burgherr et al.
2019/0336171 A1 11/2019 Lavi et al.
2020/0253640 A1 8/2020 Mullaney
2020/0352623 A1 11/2020 Stickel et al.
2020/0357501 A1 11/2020 Austin et al.
2020/0390471 A1 12/2020 Mannanal et al.
2021/0027879 A1 1/2021 Noblett et al.
2021/0038147 A1* 2/2021 Cohen .................. A61B 5/6812
2021/0077149 A1 3/2021 Edelhauser et al.

(56) References Cited

U.S. PATENT DOCUMENTS

| | | | | |
|---|---|---|---|---|
| 2021/0153944 | A1 | 5/2021 | Nikonovas | |
| 2021/0346059 | A1 | 11/2021 | Singh et al. | |
| 2021/0361322 | A1 | 11/2021 | Sun et al. | |
| 2021/0401465 | A1 | 12/2021 | Singh et al. | |
| 2022/0022963 | A1 | 1/2022 | Yu et al. | |
| 2022/0071662 | A1 | 3/2022 | Heotis et al. | |
| 2022/0093228 | A1 | 3/2022 | Austin et al. | |
| 2022/0237797 | A1 | 7/2022 | Gutmann et al. | |
| 2022/0273341 | A1 | 9/2022 | Lavi et al. | |
| 2022/0354539 | A1 | 11/2022 | Ferrante et al. | |
| 2022/0361921 | A1 | 11/2022 | Burgherr et al. | |
| 2022/0378476 | A1 | 12/2022 | Gutmann et al. | |
| 2023/0000524 | A1* | 1/2023 | Qi | A61B 17/6483 |
| 2023/0023669 | A1 | 1/2023 | Noblett et al. | |
| 2023/0086184 | A1 | 3/2023 | Noblett et al. | |
| 2023/0090626 | A1 | 3/2023 | Noblett et al. | |
| 2023/0233232 | A1 | 7/2023 | Roberts et al. | |
| 2023/0248393 | A1 | 8/2023 | Cheng et al. | |
| 2023/0255665 | A1 | 8/2023 | Pak et al. | |
| 2024/0206915 | A1 | 6/2024 | Ottoboni et al. | |
| 2024/0208014 | A1 | 6/2024 | Lorenzini et al. | |

FOREIGN PATENT DOCUMENTS

| | | | |
|---|---|---|---|
| AU | 2021228690 | A1 | 9/2022 |
| CA | 2267232 | C | 9/2009 |
| CN | 105682566 | A | 6/2016 |
| CN | 106264690 | A | 1/2017 |
| CN | 109923766 | A | 6/2019 |
| CN | 109965961 | A | 7/2019 |
| CN | 110916780 | A | 3/2020 |
| DE | 10151754 | B4 | 1/2005 |
| DE | 102015121355 | A1 | 6/2017 |
| DE | 102015121357 | A1 | 6/2017 |
| EP | 0386912 | B1 | 8/1995 |
| EP | 2152177 | B1 | 4/2011 |
| EP | 2723259 | A1 | 4/2014 |
| EP | 2117635 | B1 | 12/2015 |
| EP | 2405834 | B1 | 7/2016 |
| EP | 2767252 | B1 | 4/2019 |
| EP | 3245966 | B1 | 6/2020 |
| EP | 3776568 | A1 | 2/2021 |
| EP | 3917419 | A1 | 12/2021 |
| EP | 3503830 | B1 | 5/2022 |
| EP | 4000545 | A1 | 5/2022 |
| EP | 4034009 | A1 | 8/2022 |
| EP | 4087513 | A1 | 11/2022 |
| EP | 4110219 | A1 | 1/2023 |
| EP | 4135606 | A1 | 2/2023 |
| EP | 4192374 | A1 | 6/2023 |
| EP | 4197463 | A1 | 6/2023 |
| EP | 4226878 | A1 | 8/2023 |
| JP | H06511165 | A | 12/1994 |
| JP | 5830118 | B2 | 10/2015 |
| JP | 2019197569 | A | 11/2019 |
| KR | 101809291 | B1 | 12/2017 |
| KR | 102090906 | B1 | 3/2020 |
| KR | 102467617 | B1 | 11/2022 |
| WO | WO 9535061 | A2 | 12/1995 |
| WO | WO 2010042619 | A1 | 4/2010 |
| WO | WO 2010042619 | A4 | 6/2010 |
| WO | WO 2011026475 | A1 | 3/2011 |
| WO | WO 2011163406 | A2 | 12/2011 |
| WO | WO 2012102685 | A1 | 8/2012 |
| WO | WO 2013172800 | A1 | 11/2013 |
| WO | WO 2014163591 | A1 | 10/2014 |
| WO | 2015136544 | A1 | 9/2015 |
| WO | WO 2015142298 | A3 | 11/2015 |
| WO | WO 2016159901 | A1 | 10/2016 |
| WO | WO 2017150782 | A1 | 9/2017 |
| WO | 2017221243 | A1 | 12/2017 |
| WO | 2019195231 | A1 | 10/2019 |
| WO | WO 2019237513 | A2 | 12/2019 |
| WO | WO 2020029378 | A1 | 2/2020 |
| WO | 2020092049 | A1 | 5/2020 |
| WO | WO 2021069078 | A1 | 4/2021 |
| WO | WO 2021122701 | A1 | 6/2021 |
| WO | WO 2021142213 | A1 | 7/2021 |
| WO | WO 2021173931 | A1 | 9/2021 |
| WO | WO 2021221920 | A1 | 11/2021 |
| WO | WO 2022024133 | A1 | 2/2022 |
| WO | WO 2022031891 | A1 | 2/2022 |
| WO | WO 2022112274 | A1 | 6/2022 |
| WO | WO 2022144684 | A1 | 7/2022 |
| WO | WO 2022204096 | A1 | 9/2022 |
| WO | 2022254320 | A1 | 12/2022 |
| WO | WO 2023048948 | A1 | 3/2023 |
| WO | 2023163874 | A1 | 8/2023 |
| WO | 2023205046 | A1 | 10/2023 |
| WO | 2023230203 | A1 | 11/2023 |
| WO | 2023244586 | A1 | 12/2023 |
| WO | 2024059116 | A1 | 3/2024 |
| WO | 2024102351 | A1 | 5/2024 |
| WO | 2024102395 | A1 | 5/2024 |

OTHER PUBLICATIONS

McBride, A., et al., “The programmable hexapod: historical perspective, theoretical basis and relevance to orthopaedic practice; Bone & Joint360”, Aug. 2015, vol. 4, Issue 4, 4 pages.

Wendlandt, R, et al., “ECIFMBE 2008, IFMBE Proceedings 22”, 2008, Hamburg, Germany, pp. 1679-1682.

Bright et al, “Preliminary experience with motorized distraction for tibial lengthening; Burghardt RD: Strat Traum Limb Recon 2014”, Mar. 2014, 5 pages.

DePuySynthes, “Maxframe AUTOSTRUTTm Multi-Axial Correction System”, 2022, 2023, 4 pages.

DePuySynthes, “Maxframe AUTOSTRUTTm Multi-Axial Correction System Patient User Manual”, 2023, 10 pages.

DePuySynthes, “Maxframe AUTOSTRUTTm Multi-Axial Correction System Surgical Technique”, 2023, 64 pages.

* cited by examiner

| Date & time | Strut 1 | Strut 2 | Strut 3 | Strut 4 | Strut 5 | Strut |
|---|---|---|---|---|---|---|
| Dec. 25 2021 10AM | 114.0 | 122.8 | 104.4 | 95.1 | 144.2 | 135.3 |
| Dec. 25 2021 11AM | 114.1 | 122.9 | 104.5 | 95.2 | 144.3 | 135.2 |
| Dec. 25 2021 12AM | 114.2 | 123.0 | 104.6 | 95.3 | 144.4 | 135.1 |
| Dec. 25 2021 1PM | 114.3 | 123.1 | 104.7 | 95.4 | 144.5 | 135.0 |
| Dec. 25 2021 2PM | 114.4 | 123.2 | 104.8 | 95.5 | 144.6 | 134.9 |
| Dec. 25 2021 3PM | 114.5 | 123.3 | 104.9 | 95.6 | 144.7 | 134.8 |

FIG. 5

FAILURE DETECTION AND SENSOR BASED CONTROL IN A MOTORIZED BONE FIXATION DEVICE

CROSS REFERENCE TO RELATED APPLICATIONS

This application claims the benefit of Provisional U.S. Patent Application No. 63/524,115, filed Jun. 29, 2023, the entire disclosure of which is hereby incorporated by reference herein in its entirety.

TECHNOLOGICAL FIELD

This invention relates to controlled operation of an adjustable motorized bone fixation device, and more particularly to sensor-based control and automated detection of failure or potential failure in the device.

BACKGROUND

WO2022024133A8 discloses "A kit, including: a strut of a bone fixation device including a fixed portion and an extending portion, wherein the strut comprises a linear actuator mechanically connected to the extending portion; at least one motor adaptor coupled to the linear actuator, wherein the motor adaptor comprises a motor fastener; at least one motor unit selectively attachable and detachable from the motor fastener, wherein the motor unit is configured to functionally couple to the linear actuator and axially extend the extending portion of the strut; wherein the motor fastener is shaped and sized to receive a portion of the motor unit."

U.S. Pat. No. 11,076,801 discloses "An electrical circuitry fitted to be connected or to be an integral part of a bone fixation device having at least one linear actuator coupled between two rings, including: at least one linear actuator connector, mechanically and/or electrically connectable to said at least one linear actuator; a control circuitry, wherein said control circuitry measures a value related to the movement of said at least one linear actuator and/or to the distance or change in distance between said two rings, by receiving signals from said linear actuator connector; and a memory, wherein said memory stores said value."

GENERAL DESCRIPTION

Example 1

A control system for use with an adjustable bone fixation device having a frame connectible to bone tissue and a plurality of struts connected to the frame, the control system comprising:
- a plurality of actuators associated with the plurality of struts, each actuator configured for adjusting a length of at least one strut; and
- circuitry configured to:
  - signal the plurality of actuators to adjust the struts according to a predefined actuation plan which sets operational parameters and permitted ranges thereof;
  - determine a situation of potential failure associated with at least one actuator and involving at least one of said operational parameters being out of the permitted range; and

- implement, by signaling the at least one actuator, a recovery protocol designed to attempt completion of strut adjustment according to the predefined actuation plan.

Example 2

The control system according to Example 1, wherein the predefined actuation plan sets permitted ranges for one or more of the following operational parameters or indicators thereof:
- A. timing of adjustment;
- B. an adjustment duration;
- C. torque to be applied by the actuator onto the strut;
- D. a desired adjustment in the length of a strut.

Example 3

The control system according to Examples 1 or 2, wherein the circuitry is configured to select the recovery protocol from a plurality of recovery protocols stored in a memory of said control system.

Example 4

The control system according to Example 1, wherein the circuitry selects the recovery protocol from the plurality of recovery protocols based on one or both of: the type of operational parameter that is out of the permitted range, and the extent in which the parameter exceeds the permitted range.

Example 5

The control system according to any one of the preceding Examples, wherein the recovery protocol is designed to prevent or at least delay the control system from entering a final system error mode in which all actuators are stopped.

Example 6

The control system according to any one of Examples 3-5, wherein the plurality of recovery protocols include one or more of the following protocols or a combination thereof:
- (protocol a) waiting a preset time period, and re-attempting adjustment of the strut;
- (protocol b) moving the strut in a reciprocating motion along a predefined distance;
- (protocol c) re-attempting the adjustment that was not carried out or was only partially carried out in one or more successive actuation sessions.

Example 7

The control system according to any one of Examples 2-6, wherein the control system comprises one or more sensors configured for measuring said operational parameters or indicators thereof.

Example 8

The control system according to any one of Examples 2-7, wherein the operational parameters include parameter (C), and wherein the at least one parameter indicative of torque comprises: consumption of electrical current by the at least one actuator; operating voltage of the at least one actuator, rotation speed of the at least one actuator.

Example 9

The control system according to any one of Examples 2-8, wherein the operational parameters include parameter (D), and, wherein each actuator is associated with an encoder and the circuitry is configured to determine the change in length of the strut based on data received from the encoder.

Example 10

The control system according to any one of Examples 2-9, wherein the operational parameters include at least one of parameter (A) and parameter (B), and wherein the circuitry comprises a clock or timer for measuring the timing of adjustment or the adjustment duration respectively.

Example 11

The control system according to Example 6, wherein if (protocol a) is selected, the circuitry is configured to repeat (protocol a) a preset number of times, or until strut adjustment is completed.

Example 12

The control system according to Example 6, wherein if (protocol b) is selected, the predefined distance along which the strut is moved is between 0.01 mm to 2 mm.

Example 13

The control system according to Example 6, wherein if (protocol a) is selected and following said preset number of times movement of the strut is not completed, the circuitry is configured to generate one or both of: a failure alert, instructions to the patient or caregiver.

Example 14

The control system according to Example 6, wherein if (protocol c) is selected, a planned adjustment in the one or more successive sessions is modified to include the adjustments that was not carried out or was only partially carried out.

Example 15

The control system according to any one of the preceding Examples, wherein the circuitry comprises one or more sensors configured for sensing conditions that are associated with one or both of the device and its surroundings, the one or more sensors including: a temperature sensor; a humidity sensor; a sensor configured for detecting the current posture of the patient; a sensor configured for detecting a current orientation of the body part to which the device is connected; an acceleration sensor; a weight/load sensor.

Example 16

The control system according to Example 15, wherein the circuitry is configured to check, upon entering a treatment mode, whether the conditions sensed by the one or more sensors are within a permitted range.

Example 17

The control system according to Example 15 when according to Example 6, wherein the plurality of recovery protocols further include (protocol d): delaying adjustment of the strut and re-attempting it when at least one of:

(a) the one or more sensors detect a desired change in at least one of the conditions;
(b) the conditions sensed by all of said one or more sensors are within a permitted range.

Example 18

The control system according to any one of Examples 15-17, wherein the circuitry is configured to select the recovery protocol from a plurality of recovery protocols while taking into account at least one reading obtained by said one or more sensors.

Example 19

The control system according to any one of Examples 6-18, where in the circuitry is configured to implement more than one recovery protocol, and to stop when either adjustment of the strut is completed or a predefined time period passed.

Example 20

The control system according to any one of the preceding Examples, wherein the circuitry is configured to identify whether the potential failure is associated with a single actuator or is associated with multiple actuators.

Example 21

The control system according to Example 20, wherein if the potential failure is associated with a single actuator, the circuitry controls operation of the plurality of actuators according to one or more of the following:

(A) continue operation of all actuators except for the actuator for which potential failure had been indicated;
(B) carry out the recovery protocol for the actuator for which potential failure had been indicated, and only then continue operation of all actuators;
(C) stop operation of all actuators.

Example 22

The control system according to any one of the preceding Examples, wherein each actuator comprises an electric motor.

Example 23

The control system according to Example 22, wherein said motor is a brushed or brushless DC motor.

Example 24

The control system according to any one of the preceding Examples, wherein the circuitry comprises a memory in which the predefined actuation plan, permitted operation and condition ranges and the plurality of recovery protocols are stored.

Example 25

The control system according to any one of the preceding Examples, wherein the circuitry is in communication with at least one external device, and is configured to notify the at least one external device at least when recovery had not succeeded.

Example 26

The control system according to Example 25, wherein the external device is a cell phone of the patient, a physician, or a caregiver.

Example 27

The control system according to any one of the preceding Examples, wherein the circuitry is configured to one or both of suggest and effect changes in the actuation plan for compensating for a recovery protocol which involves a delay in strut adjustment.

Example 28

An adjustable bone fixation device, comprising:

a frame connectible at least indirectly to bone tissue and comprising at least two spaced apart portions;

a plurality of struts extending between the at least two portions of the frame; and the control system according to Example 1, whereby the plurality of actuators are operably connected to the plurality of struts.

Example 29

The device according to Example 28, wherein the two spaced apart portions of the frame constitute of two rings; and wherein adjustment of the struts modifies a distance between the rings and thereby a position and/or orientation of the rings with respect to each other and/or with respect to the bone tissue.

Example 30

The device according to Example 28 or Example 29, wherein each of the plurality of actuators is directly connected to its associated strut such that torque generated by the actuator is directly correlated with linear force required to extent the linear adjustment of the strut.

Example 31

The device according to any one of Examples 28-30, wherein the circuitry comprises a control unit, a housing of the control unit being mounted onto one of the spaced apart portions of the frame.

Example 32

A method of operating a control system of an adjustable bone fixation device, the device comprising a plurality of struts connected to a frame, each strut associated with an actuator which is configured to adjust the strut, the method comprising:

controlling the actuators for adjusting the struts according to a predefined actuation plan which sets operational parameters and permitted ranges thereof;

determining a situation of potential failure associated with at least one actuator and involving at least one of said operational parameters being out of the permitted range; and implementing, by signaling the at least one actuator, a recovery protocol designed to attempt completion of strut adjustment according to the predefined actuation plan.

Example 33

The method according to Example 32, wherein the predefined actuation plan sets permitted ranges for one or more of the following operational parameters or indicators thereof:

A. timing of adjustment;

B. an adjustment duration;

C. torque to be applied by the actuator onto the strut;

D. a desired adjustment in the length of a strut.

Example 34

The method according to Example 33, further comprising selecting the recovery protocol from a plurality of recovery protocols stored in a memory of said control system.

Example 35

The method according to any one of Examples 32-34, wherein the recovery protocol is designed to prevent or at least delay the control system from entering a final system error mode in which all actuators are stopped.

Example 36

The method according to any one of Examples 32-35, wherein the plurality of recovery protocols include one or more of the following protocols or a combination thereof:

(protocol a) waiting a preset time period, and re-attempting adjustment of the strut;

(protocol b) moving the strut in a reciprocating motion along a predefined distance;

(protocol c) re-attempting the adjustment that was not carried out or was only partially carried out in one or more successive actuation sessions;

(protocol d) re-attempting adjustment of the strut when one or more sensors of the control system detect a desired change in at least one condition.

Example 37

The method according to any one of Examples 32-36, further comprising, prior to controlling the actuators for adjusting the struts, checking if conditions sensed by one of more sensors of the control system are within their permitted ranges.

Example 38

The method according to any one of Examples 32-37, wherein said conditions include one or more of: temperature, pressure, load/weight, acceleration.

Example 39

A computer program product embodied on a computer readable medium and configured to implement the method of any one of Examples 32-38.

Example 40

A control system for use with an adjustable bone fixation device having a frame connectible to bone tissue and a plurality of struts connected to the frame, the control system comprising:
- a plurality of actuators associated with the plurality of struts, each actuator configured for adjusting a length of at least one strut;
- a plurality of sensors configured for sensing one or more of the following conditions:
- pressure, temperature, load, acceleration; and circuitry configured to:
- receive indications from the one or more sensors regarding the sensed conditions;
- determine whether the sensed conditions are within their permitted range;
- if at least one of the sensed conditions is outside its permitted range, delay or retry adjustment of the struts;
- when all sensed conditions are within their permitted range, automatically activate the plurality of actuators to adjust the struts.

Example 41

The control system according to Example 40, wherein if at least one of the sensed conditions is outside its permitted range, the circuitry is configured to issue one or both of: an alert regarding the sensed condition, instructions to the patient or caregiver.

Example 42

The control system according to Example 40 or Example 41, wherein when all sensed conditions are within their permitted range, the circuitry is configured to signal the plurality of actuators to adjust the struts according to a predefined actuation plan which sets operational parameters for the actuators and permitted ranges thereof.

Example 43

The control system according to any one of Examples 40-42, wherein the circuitry is configured to one or both of suggest and effect changes in the predefined actuation plan to compensate for the delayed adjustment.

Example 44

The control system according to any one of Examples 40-43, wherein the circuitry is further configured to: determine a situation of potential failure associated with at least one actuator and involving at least one of said operational parameters being out of the permitted range; and implement, by signaling the at least one actuator, a recovery protocol designed to attempt completion of strut adjustment according to the predefined actuation plan.

Example 45

A control system for use with an adjustable bone fixation device having a frame connectible to bone tissue and a plurality of struts connected to the frame, the control system comprising:
- a plurality of actuators associated with the plurality of struts, each actuator configured for adjusting a length of at least one strut;
- a control unit comprising circuitry configured to signal the plurality of actuators to adjust the struts;
- the control unit having a sealed housing; and at least one pressure sensor located inside the sealed housing;
- wherein the circuitry is configured to receive indications from the at least one pressure sensor to determine whether the sealing had been breached.

Example 46

The control system according to Example 45, wherein the circuitry is configured to compare a current pressure indication with an original pressure measured during manufacturing of the control unit.

Example 47

The control system according to Example 45 or Example 46, wherein if the sealing had been breached, the circuitry is configured to issue one or both of: an alert, and instructions to the patient or caregiver to keep the bone fixation device away from liquids.

Example 48

The control system according to any one of Examples 45-47, wherein the sealed housing is impermeable to air and water.

Example 49

A control system for use with an adjustable bone fixation device having a frame connectible to bone tissue and a plurality of struts connected to the frame, the control system comprising:
- a plurality of actuators associated with the plurality of struts, each actuator configured for adjusting a length of at least one strut;
- a control unit comprising circuitry configured to signal the plurality of actuators to adjust the struts;
- the control unit having a selectively permeable housing which allows air to flow through; and
- at least one pressure sensor located inside the housing;
- wherein the circuitry is configured to receive indications from the at least one pressure sensor to determine whether the pressure is within a permitted range.

Example 50

The control system according to Example 49, wherein if the pressure is outside its permitted range, the circuitry is configured to delay adjustment of the struts until the pressure is within the permitted range.

Example 51

The control system according to Example 49 or Example 50, wherein the housing is formed of an air permeable and water resistant material.

Example 52

The control system according to Example 49 or Example 50, wherein the housing is formed of a non-permeable material, but comprises one or more openings, each opening including a valve which enables air to flow through and prevents water from entering.

As referred to herein, a "potential failure" may refer to a situation in which normal operation of a control system of an automated bone fixation device is interfered, for example, in which at least one actuator is prevented or delayed from completing a preplanned adjustment of the associated strut. Examples of potential failure situations include: a situation in which an actuator is about to fail or malfunction (e.g. mechanically, electrically); a situation in which adjustment of a strut is interrupted or prevented, for example due to an obstruction or an obstacle (e.g. an external object being stuck in the movement path of the strut and/or of the device frame); a situation in which external conditions slow or prevent the operation of the actuator, for example, excess load is exhibited on the device (e.g. if the patient applies high weight bearing or impact on the treated limb), extreme temperatures affect operation of the actuator, e.g. cause overheating.

As referred to herein, a "recovery protocol" refers to a set of operations or steps carried out automatically by the control system in response to an identified situation of potential failure. The recovery protocol is intended to overcome the identified situation, for example so as to allow the control system to complete any missed or partial adjustment and to return to normal operation (e.g. to return to operation according to a predefined actuation plan). The recovery protocol is designed so that adjustment of a strut is completed, even if completion (e.g. the strut reaching a designated length) occurs at a later time than initially planned. The recovery protocol is designed to resolve the situation of potential failure, thereby making the situation only temporary (e.g. as opposed to reaching a final system error mode). Generally, the recovery protocol can be of an "active" type, involving, for example, moving the strut in a reciprocating motion, as further described below; or of a "passive" type, involving, for example, waiting a certain time period, as further described below.

BRIEF DESCRIPTION OF THE DRAWINGS

In order to better understand the subject matter that is disclosed herein and to exemplify how it may be carried out in practice, embodiments will now be described, by way of non-limiting examples only, with reference to the accompanying drawings, in which:

FIG. 5 is an example of an actuation plan for adjustment of a plurality of struts of the bone fixation device, according to embodiments of the presently disclosed subject matter;

DETAILED DESCRIPTION OF EMBODIMENTS

Figure 1:
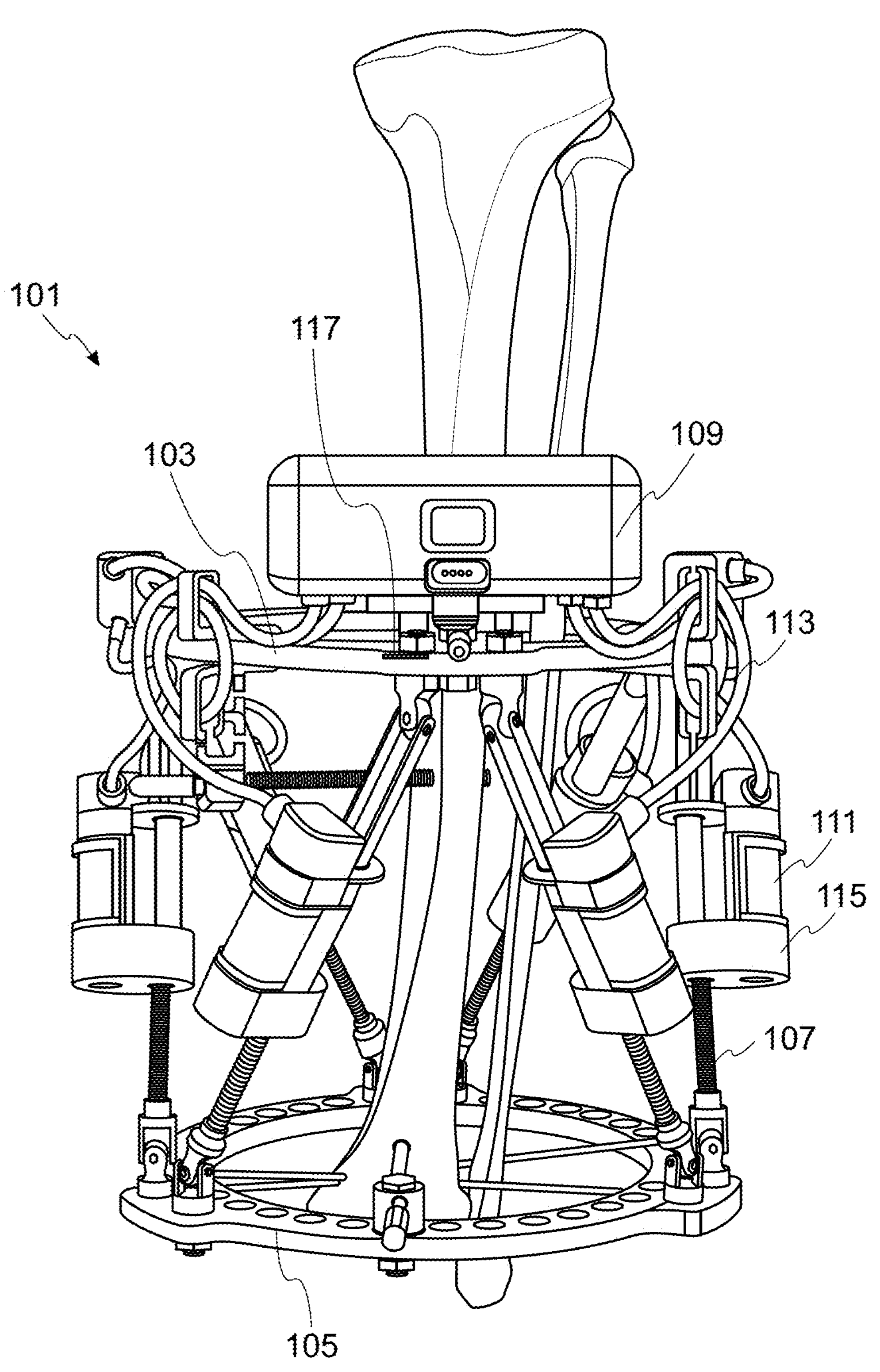
FIG. 1 illustrates an adjustable bone fixation device connected to a bone, according to embodiments of the presently disclosed subject matter.

FIG. 1 illustrates an adjustable bone fixation device connected to a bone, according to embodiments of the presently disclosed subject matter.

Bone fixation device 101 is generally intended to be connected to the bone of a patient, in a surgical process. In some cases, the device is used for the treatment of a fractured bone, misaligned bone(s), a deformed bone, a bone that needs to be changed in length, and/or other orthopedic or generally bone related conditions.

The bone fixation device is generally comprised of a frame constituting of at least two portions, 103 and 105, and a plurality of struts 107 (e.g. 1, 2, 4, 5, 8, 10 or intermediate or larger number of struts), connecting the at least two portions of the frame. In some embodiments, as shown, the bone fixation device is shaped as a hexapod, and the two frame portions are formed as two rings having six struts which interconnect the rings. In other embodiments, the two frame portions may include open rings, arc shaped frames, horseshoe shaped frames, rods, and/or otherwise shaped frame portions.

In some embodiments, the two portions of the frame are at least partially connected to the bone via pins (e.g. transfixation pins), rods, wires (e.g. k-wires), or other suitable fixation elements which extend from the frame portion and into the bone. Adjustment of the struts, such as by lengthening or shortening a strut along a linear axis, modifies the distance between the two frame portions (e.g. by pulling on the frame portions towards each other or by pushing the frame portions away from each other. In an example, shortening of struts can approximate the two frame portions towards each other; lengthening of struts can distance the two frame portions away from each other Adjustment of the struts can also modify the relative position and/or orientation of the two frame portions (and the bone portions to which the frame portions are attached) with respect to each other, for example, shortening of some of the struts and/or lengthening of some of the struts can change an angular orientation of the frame portions with respect to each other (for example, when the frame portions consist of rings, change the plane in which the ring lies and/or change a rotational positioning of the ring).

Automated adjustment of the bone fixation device is carried out, in accordance with some embodiments, by a control system which is operably connected to the device. The control system is generally comprised of a control unit 109 and a plurality of actuators 111, such as motors (e.g. linear motors). In some embodiments, each of the actuators is associated with a single strut and is configured to drive the adjustment of the specific strut. In some embodiments, the control unit is electrically connected to the actuators via cables 113. (Additionally or alternatively, a wireless connection may be established between the control unit and the actuators).

In some embodiments, each of the actuators is maintained within a designated adaptor 115 which holds the actuator in an operable coupling with the strut. In some embodiments, the adaptor is shaped to maintain the actuator axially aligned with the strut which the actuator adjusts. Alternatively, in some embodiments, an actuator may be contained (e.g. embedded) within the strut itself.

In some embodiments, the control system of the bone fixation device comprises one or more sensors, for example: sensors configured for obtaining system related measurements, such as for measuring operational parameters of the actuators (e.g. torque generated by an actuator, current consumption, operation voltage, rotation speed of the actuator, etc.); and/or sensors configured for obtaining measurements related to the surroundings, such as for measuring environmental conditions (e.g. temperature, humidity), measuring a load or impact on the device, measuring a posture of the patient, etc. FIG. 1 shows an example of a sensor 117 for measuring load acting on the device, positioned, for example, at an attachment area of a strut to the top frame portion.

It is noted that while a hexapod external fixation device is shown herein, other bone fixation devices such as a monorail are also contemplated.

Figure 2:
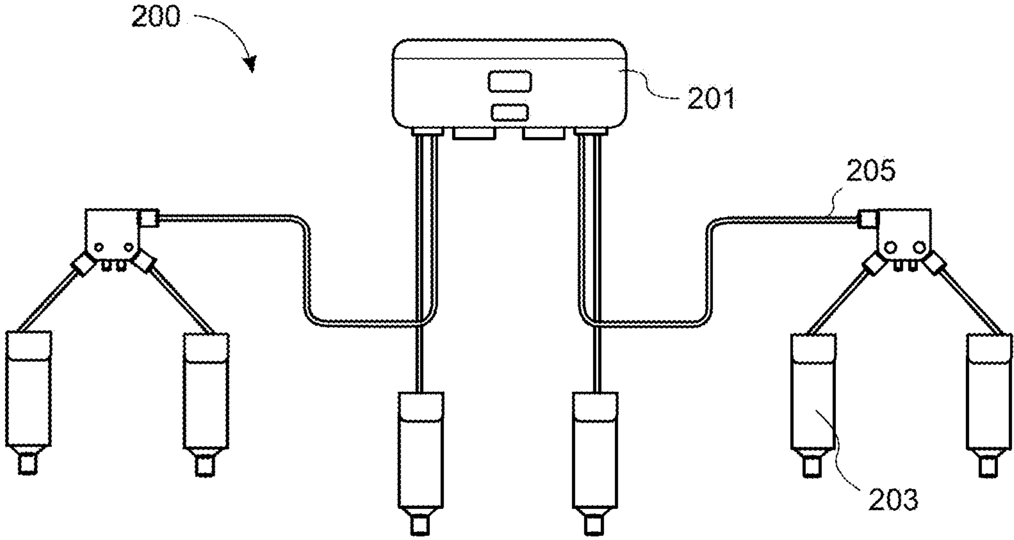
FIG. 2 illustrates a control system for use with an adjustable bone fixation device, according to embodiments of the presently disclosed subject matter.

FIG. 2 illustrates a control system for use with an adjustable bone fixation device, according to embodiments of the presently disclosed subject matter.

A control system 200 as shown generally comprises a control unit 201, comprising a housing in which computational, processing, communication and/or memory means are contained. The control unit is operably connected to a plurality of actuators 203, optionally, via cables 205 or other suitable wiring. In some embodiments, each of the actuators is comprised of a motor, for example, a brush DC motor or a brushless DC motor.

In some embodiments, control unit 201 comprises a power source (not shown), for example an electric power source. In some embodiments, the power source comprises a battery, for example a non-replaceable battery or a replaceable battery or a rechargeable battery. In some embodiments, the control unit delivers electric power from the power source to each of the actuators via the cables. Optionally, the battery is sufficient to power the device for as long as the bone fixation device is required to stay connected to the bone, for example, for a time period of between 1-3 months.

In some embodiments, in use, the control system is coupled to the frame and the struts of the bone fixation device. In some embodiments, each actuator is operably connected to a strut such that activation of the actuator generates torque for adjusting the strut. In an example, the actuator rotates a gear or a gear train which is operably coupled to at its end to a threaded lead screw. Movement of the lead screw linearly shortens or lengthens the strut by extending or contracting an adjustable segment of the strut. It is noted that other mechanisms may be used for adjusting the strut, for example, a hydraulic mechanism, a spring-based mechanism, a magnetic mechanism, and/or other mechanism suitable for extending or contracting an adjustable segment of the strut.

In embodiments in which the actuator is external to the strut, the actuator may be held by an adaptor or other suitable restraining means for coupling the actuator to the struts. In embodiments in which the actuator is embedded within the strut, a connector may be used for connecting the control unit (such as via the cables or other wiring) to the embedded actuator.

In some embodiments, the control unit housing is removably connected to the frame, for example via fasteners.

In some embodiments, an actuation plan is uploaded (or otherwise communicated) to the control unit, in which it can be stored (for example, in a memory of the control unit). Optionally, an actuation plan is communicated to the control unit over the network.

The actuation plan is designed to carry out a treatment regimen, which can be determined based on a diagnosis of the patient (for example, using the results of tissue imaging); based on patient parameters (e.g. age, level of physical activity); based on the required bone modification; and/or other factors.

In some embodiments, the actuation plan sets parameters according to which the control system operates the actuators. The parameters can be set for each actuator separately, or for multiple actuators together. The parameters can be set per a single actuation session, or per multiple actuation sessions together.

Operational parameters set by the actuation plan can include, for example:

a. Timing of actuation (e.g. an actuation schedule, time intervals (or permitted ranges) between actuation sessions, specific times (or permitted ranges) for initiating and/or for completing an actuation session, a total time period over which device adjustment should be performed (e.g. 1 day, 1 week, 6 weeks, 1 month, 3 months), and/or other time related parameters);
b. An actuation session duration or a permitted range thereof;
c. A torque range or limit to be generated by an actuator; and/or other operational parameters of the actuator which affect, directly or indirectly, the axial adjustment of the strut, such as: current consumption of the actuator, voltage, rotation speed of the actuator, or other.
d. A desired change in the length of a strut or a permitted range thereof, for example, a length measured along the strut between the end attachments of the strut to the two portions of the frame.
e. A travel range of a strut, for example, a total distance along which the strut is planned to be adjusted.

Figure 3:
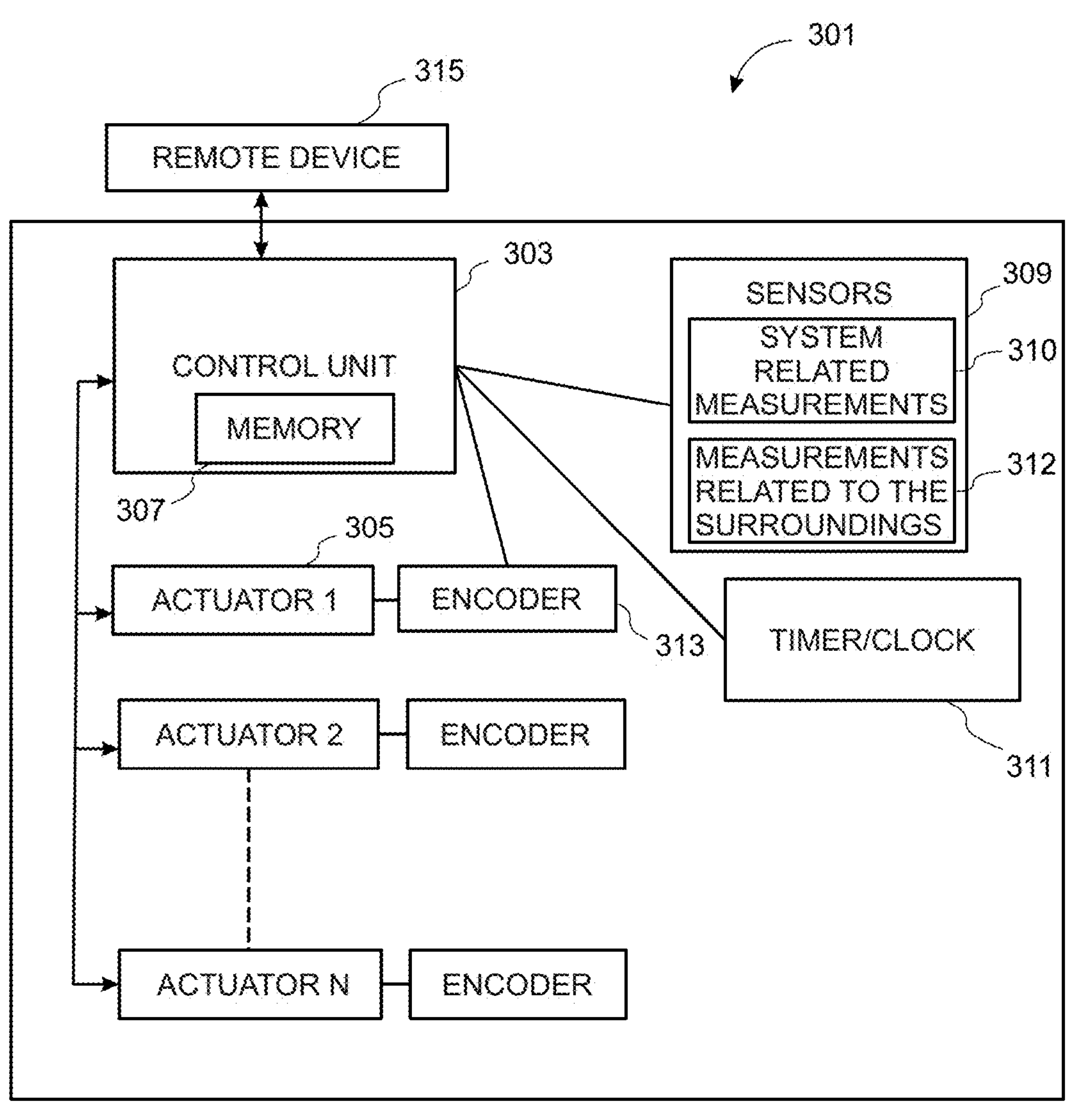
FIG. 3 is a block diagram of a control system for use with an adjustable bone fixation device, according to embodiments of the presently disclosed subject matter.

FIG. 3 is a block diagram of a control system for use with an adjustable bone fixation device, according to embodiments of the presently disclosed subject matter.

As described hereinabove, in some embodiments, control system 301 includes a control unit 303 for controlling the plurality of actuators 305. In some embodiments, the control unit operates the actuators according to an actuation plan stored at a memory 307 of the control unit.

In some embodiments, control unit 303 is configured to obtain readings from one or more sensors 309 of the system.

In some embodiments, the sensors 309 include one or more sensors 310 that are configured for measuring system-related parameters, such as actuator-related parameters, for example, measure the torque generated by the actuator which is indicative of the axial force applied onto the strut. In some cases, one or more sensors are configured for measuring the torque and/or a parameter indicative of the torque, for example, for measuring the current consumption of the actuator (e.g. a current meter or sensor). Since in some embodiments the actuator is configured to directly drive the adjustment of the strut, a correlation exists between consumption of electrical current by the actuator and the torque generated the actuator (e.g. when brushed motors are used), and/or between the rotation speed of the actuator and voltage, and the torque generated by the actuator (e.g. when brushless motors are used). In some embodiments, sensors 309 include one or more sensors 312 that are configured for measuring conditions related to the surroundings of the device, and/or to external factors which may have an effect on device operation. Examples of such sensors include: a temperature sensor and/or a humidity sensor, since, for example, extreme temperature conditions may affect operation of the actuator and/or of the circuitry;

- a sensor configured for detecting the current posture of the patient, since, for example, in a patient standing up the load acting on the device would be higher as compared to when the patient sits or lies down;
- a sensor configured for detecting a current orientation of the body part to which the device is connected, since, for example strut adjustment and/or actuator operation may be affected by the orientation and/or the load acting on the device in a certain orientation;
- an acceleration sensor or an impact sensor, since, for example, it would be preferred to adjust the strut whilst the patient is still and not moving;
- a weight/load sensor.

The sensors may be positioned with respect to the bone fixation device based on their function, for example, a weight/load sensor can be positioned between a strut and the frame portion to which it is connected and/or within the strut itself, so as to identify the load acting on it; a temperature/humidity sensor can be positioned externally on the frame portions, and/or positioned with respect to the control system (e.g., embedded within or mounted on a housing of the control unit, embedded within or mounted on a housing of an actuator); a pressure sensor may be located inside the control unit, as further described below; or other sensor positions suitable for sensing one or both of device-related parameters and environmental conditions.

Referring back to the block diagram, in some embodiments, the system includes a timer and/or a clock 311, which can be utilized by the control unit for timing operation of the actuators according to the actuation plan; for monitoring a duration of actuation and/or monitoring the time it takes to complete a planned adjustment of a strut; monitoring a time interval between successive actuations; and/or other time or timing related factors.

In some embodiments, each of the actuators is coupled to an encoder 313, which is in communication with the control unit. The encoder tracks the speed and/or position of the moving part (e.g. shaft, rotor) of the actuator. Based on the feedback received from the encoder, control unit 303 can determine the change in the length of the strut, and/or a relative position of the strut, and/or a speed in which the strut is adjusted.

In some embodiments, based on input received from the sensors, the clock/timer, and/or the encoder(s), the control unit is configured to determine the extent of adjustment and to identify whether the adjustment had been carried out according to the actuation plan.

In some embodiments, one or more components of the control system 301, for example the control unit 303, are in communication with a remote or external device 315. The remote device may include a cellular phone, a wearable device, a remote computer, a tablet, a remote server, an information storage cloud. In some cases, the control system communicates with a remote device of the patient or a caregiver, a physician, or other.

Figure 4:
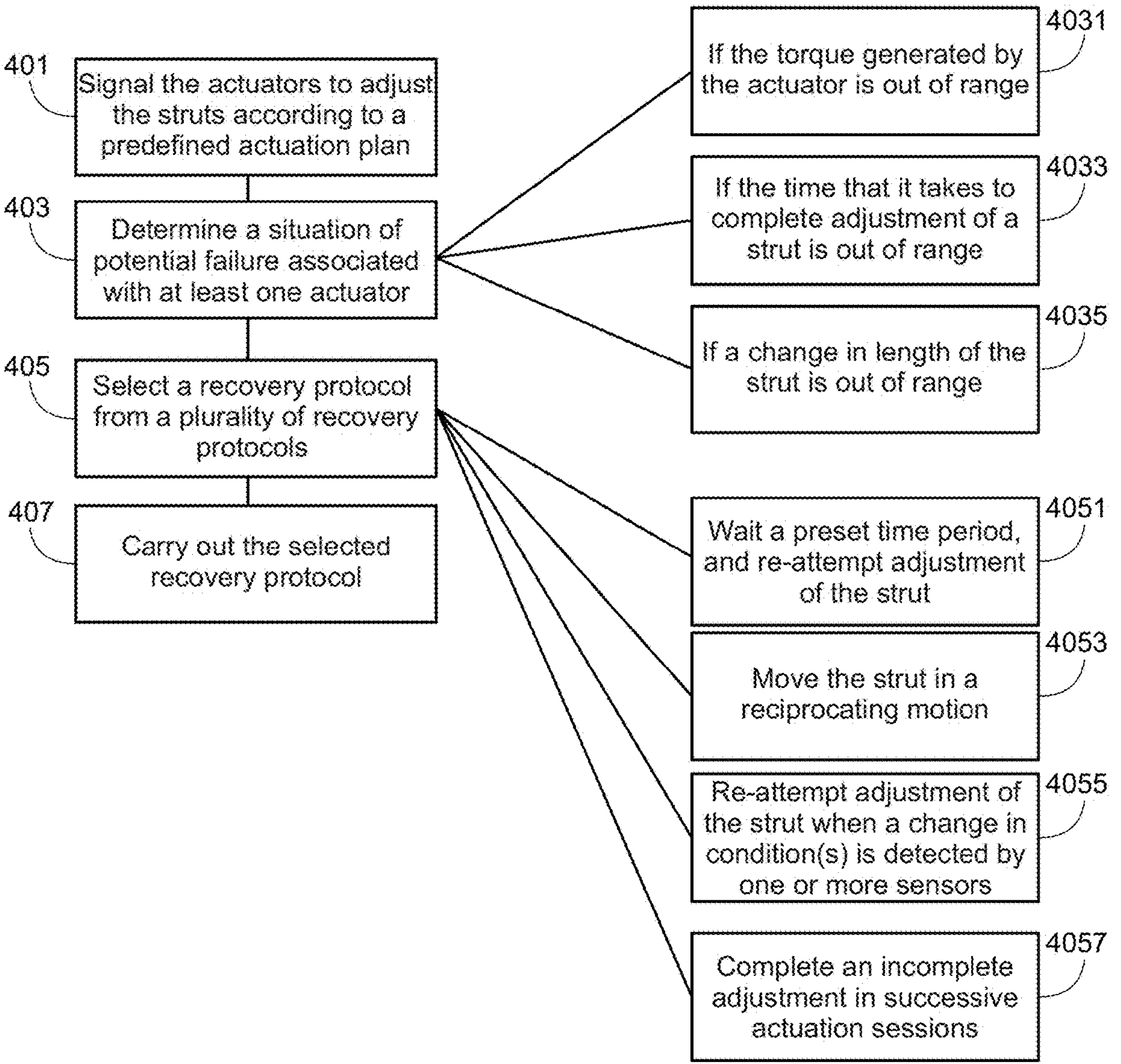
FIG. 4 is a flowchart of a method of determining potential failure associated with at least one actuator of the control system and implementing a recovery protocol, according to embodiments of the presently disclosed subject matter.

FIG. 4 is a flowchart of a method of determining potential failure associated with at least one actuator of the control system and implementing a recovery protocol, according to embodiments of the presently disclosed subject matter.

At 401, the control system signals the plurality of actuators to adjust the struts according to a predefined actuation plan, for example as described herein.

At 403, a situation of potential failure associated with at least one actuator is determined. In some embodiments, the system's control unit is configured to determine potential failure when one or more of the operational parameters set by the actuation plan are out of range. For example:

- if the torque generated by the actuator (and/or an indicator of the torque, such as current consumption) is out of range (4031). For example, the torque is a stall torque level; the current consumption reaches a current stall level.
- if the time that it takes to complete adjustment of the strut is out of range (4033), for example, the time is shorter, for example, than 3 seconds, 1 seconds, 5 seconds; or is longer, for example, than 10 seconds, 15 seconds, 13 seconds.
- if the change in length of the strut (for example determined using data obtained by an encoder coupled to the actuator) is out of the range defined by the actuation plan (4035), for example, the change is lower than 0.01 mm.

In some embodiments, when potential failure was identified and before selecting and implementing a recovery protocol, the control system checks whether the strut reached its target length and/or its end position, for example based on data received from the encoder. If it is determined that the strut is at its target length (and/or end position), then the system may decide to directly enter an error mode, without the implementation of a recovery protocol.

At 405, a recovery protocol is selected out of a plurality of recovery protocols, for example stored in the system memory. Some examples of recovery protocols include the following protocols or a combination thereof:

- waiting a preset time period, and then re-attempting adjustment of the strut (4051). For example, try adjusting again after 1 second, 5 seconds, 1 minute, 5 minutes, or intermediate, longer or shorter time periods.
- moving the strut in a reciprocating manner (4053), preferably starting from an adjustment in an opposite direction than the direction defined by the actuation plan (e.g., if the strut was to be lengthened, it would first be shortened and only then lengthened, optionally in a repeatable manner). Optionally, the strut is extended and shortened repetitively along a distance, for example a distance shorter than 0.1 mm, shorter than 0.05 mm, shorter than 0.01 mm. Additionally or alternatively, the strut can be moved back and forth as a single unit, for example along a predefined distance, e.g. 0.1 mm, and optionally repetitively. The reciprocating movement is generally performed along a distance which is short enough so as not to have a clinical effect on the bone. A potential advantage of the reciprocating movement may include that an obstacle interfering with the adjustment may be pushed away by the movement or otherwise overcome.

re-attempting adjustment of the strut when a change in condition(s) is detected by the one or more sensors of the system (4055). For example, if the actuator operation was affected by an extreme temperature (e.g., warm weather or direct sunlight which caused the actuator temperature to rise), then an indication of a lower temperature or a drop in temperature, as sensed by a temperature sensor of the system, may be a trigger for reattempting adjustment of the strut. In another example, if the actuator operation is affected by overload (e.g., if the patient is in a posture in which the device needs to withstand additional loads), then an indication of a lower load/weight or a reduction thereof as sensed by a load/weight/acceleration/force sensor of the system may be a trigger for reattempting adjustment of the strut. In another example, if an acceleration or impact sensor sense a change or value which is correlated with patient movement, the control system may wait until the patient is still and then re-attempt adjustment of the strut.

In some cases, the system senses conditions (e.g. temperature, load, acceleration, etc.) to determine if the conditions are in a permitted, predefined range in which treatment can be carried out. Conditions that are out of the permitted range may have one or both of clinical effects (for example, a low temperature can be associated with stiffer tissues that are harder to move) and operational effects (for example, a load acting on the device can cause an actuator to apply excessive unneeded force). An exemplary feedback loop of the system circuitry, which is based on sensed conditions, is described below with respect to FIG. 6. In some embodiments, the feedback loop of FIG. 6 can be initiated prior to initiation of the method of FIG. 4, or can override it. In other words, the system can be configured to first check if all sensed conditions (e.g. temperature, acceleration, load, pressure, etc.) are within their permitted ranges, and only then signal the actuators to adjust the struts. Then, the method of FIG. 4 can be carried out for determining if a situation of potential failure of at least one actuator exists. In some embodiments, the sensed conditions are re-checked during the actuation session itself, and/or at an end thereof.

completing an incomplete adjustment of a strut in one or more successive actuation sessions (4057).

In some cases, a specific recovery protocol is selected based on the type of parameter(s) which were out of range, and based on the extent in which a parameter exceeds the permitted range. In a first example, if the torque is out of range and exceeds a predefined threshold (or an indicator of the torque exceeds a threshold), this may imply that an obstruction is in the way of the strut and/or the actuator, causing a rise in the torque generated by the actuator. In such potential failure situation, the control unit may select a recovery protocol which includes a reciprocating movement (which may contribute to overcoming the obstruction and/or releasing the obstruction). Additionally or alternatively, the control unit may select a recovery protocol in which adjustment is attempted again after a certain time period, during which the obstruction may had been removed. In a second example, if the change in length of the strut is out of the range defined by the actuation plan, for example, the strut was extended only a partial length, this may imply that the patient's current posture is interfering with completion of the adjustment. In such potential failure situation, the control unit may select a recovery protocol in which strut adjustment is attempted again only once an indication is received from a sensor of the system (e.g. a load sensor and/or force sensor and/or acceleration sensor and/or weight sensor) suggesting that the posture changed and it would now be possible to extend the strut to the full length. In some cases, more than one recovery protocol can be applied, for example, two types of recovery protocols can be performed one after the other, for example if the first recovery protocol did not result in completion of strut adjustment. In some cases, recovery protocols can be combined, for example, the control unit initiates a reciprocating movement protocol, while at the same time awaiting an indication of a change in conditions to be received from the plurality of sensors. Optionally, once the indication of change in conditions is received, the preplanned adjustment of the strut is attempted again.

In some cases, the control unit selects an initial recovery protocol without obtaining data from the sensors. Optionally, if/when data is obtained from the sensors, the control unit decides to apply a different recovery protocol and/or prioritizes the recovery protocols to be applied based on the obtained data.

In some embodiments, prior to selecting and implementing a recovery protocol, the control unit checks whether the potential failure is associated with a single actuator, or whether multiple actuators are involved. This can be checked for example by activating all actuators, optionally simultaneously, to try and move their associated struts.

In some cases, failure of a single actuator is associated with a technical (e.g. mechanical) failure; while failure of multiple actuators may indicate a clinically related issue, for example, in which the bone(s) affect the device operation, and/or a load acts on the device.

In some embodiments, if only a single actuator is involved, the control unit can continue operation of the rest of the actuators except for the actuator for which potential failure had been indicated; and/or carry out a recovery protocol for the actuator for which potential failure had been indicated (optionally whilst stopping the other actuators until the failing actuator had recovered).

In some cases, if a potential failure situation is identified (e.g., based on one or more of the above mentioned operation parameters being out of range) but the length of the strut or of an adjustable segment thereof is at its target length or sufficiently close thereto, the control system may be configured not to apply any recovery protocols. Optionally, an alert is issued to a human operator (e.g., a patient, physician, caregiver) via the control unit and/or communicated to the external device. In an example, when potential failure is identified, the control unit compares a current length and/or position of the strut (e.g., based on data received from the encoder) to a planned length and/or position for the strut. Optionally, the control unit checks if an adjustable segment of the strut is already extended to its maximum length (or shortened to its minimum length). In such case, the control unit can decide not to implement a recovery protocol, and optionally to issue an error alert.

At 407, the selected recovery protocol(s) are carried out, for example by the control unit signaling the plurality of actuators according to the recovery protocol. In some cases, if the applied recovery protocol(s) does not result in completion of strut adjustment, for example after a certain time period (e.g., 15 minutes, 30 minutes, 2 hours, 1 day, or intermediate, longer or shorter time periods), the system enters an error mode, and the actuators are fully stopped. Optionally, an alert is issued to a human operator (e.g., a patient, physician, caregiver) via the control unit and/or communicated to the external device.

Implementation of the recovery protocol may prevent or at least delay the control system from entering a final system error mode in which all actuators are stopped, and device operation is ceased. Also, by identifying potential failure in real time and implementing a recovery protocol, overheating and/or damage to the actuator may be reduced or prevented.

Another potential advantage of implementing a recovery protocol may include reducing or avoiding involvement of external human operators (such as the patient themselves, the physician, the caregiver etc.), allowing the system to return to normal operation, for example without requiring the external operator to actively resume operation. Automated recovery may reduce interruption or inconvenience to the patient, since the control system can be capable of independently overcoming situations which, in the absence of a recovery protocol, may have caused the system to cease operation, requiring attention and handling thereof.

In some embodiments, if there is a delay in strut adjustment, (for example due to a selected recovery protocol which involves a wait period), the control system can compensate for the delay, for example by changing the actuation plan (and/or suggesting a change in the plan, for example for approval by the user, physician, or other). The compensation can be achieved, for example, by increasing the length by which the strut is adjusted, by increasing the duration of adjustment, by increasing the rate of adjustment, adding another adjustment session to the schedule (e.g. intermediate other scheduled sessions, or at the end of the planned scheduled sessions. In an example, if the delay causes a scheduled adjustment to be pushed to a time which overlaps with the next scheduled adjustment, compensation can be achieved by increasing the length by which the strut is adjusted at the later scheduled adjustment—for example, instead of adjusting by 0.1 mm at each of the scheduled adjustments—adjusting by 0.2 mm once during the later adjustment session.

FIG. 5 is an example of an actuation plan for adjustment of a plurality of struts of the bone fixation device, according to embodiments of the presently disclosed subject matter.

In some embodiments, the actuation plan defines, for the plurality of actuators, one or more parameters based on which operation of the actuator is carried out. Such parameters include, for example:

- the length by which the strut associated with the actuator should be lengthened or shortened;
- the total length of the strut following adjustment;
- the adjustment initiation time and/or designated completion time;

In the example shown, a single day actuation plan is presented. The actuation plan defines for each of six struts and for each actuation session the designated completion time of the adjustment, and the length by which the strut needs to be length or shortened.

In an exemplary actuation plan, 1-20 actuation sessions are carried out in a single day. The total length by which the strut is adjusted over a day is, for example, up to 1 mm. In each actuation session, the strut is adjusted by, for example, 0.05 mm to 1 mm. A duration of each actuation session ranges, for example, between 2-10 seconds, e.g. 3 seconds, 5 seconds, 8 seconds.

Figure 6:
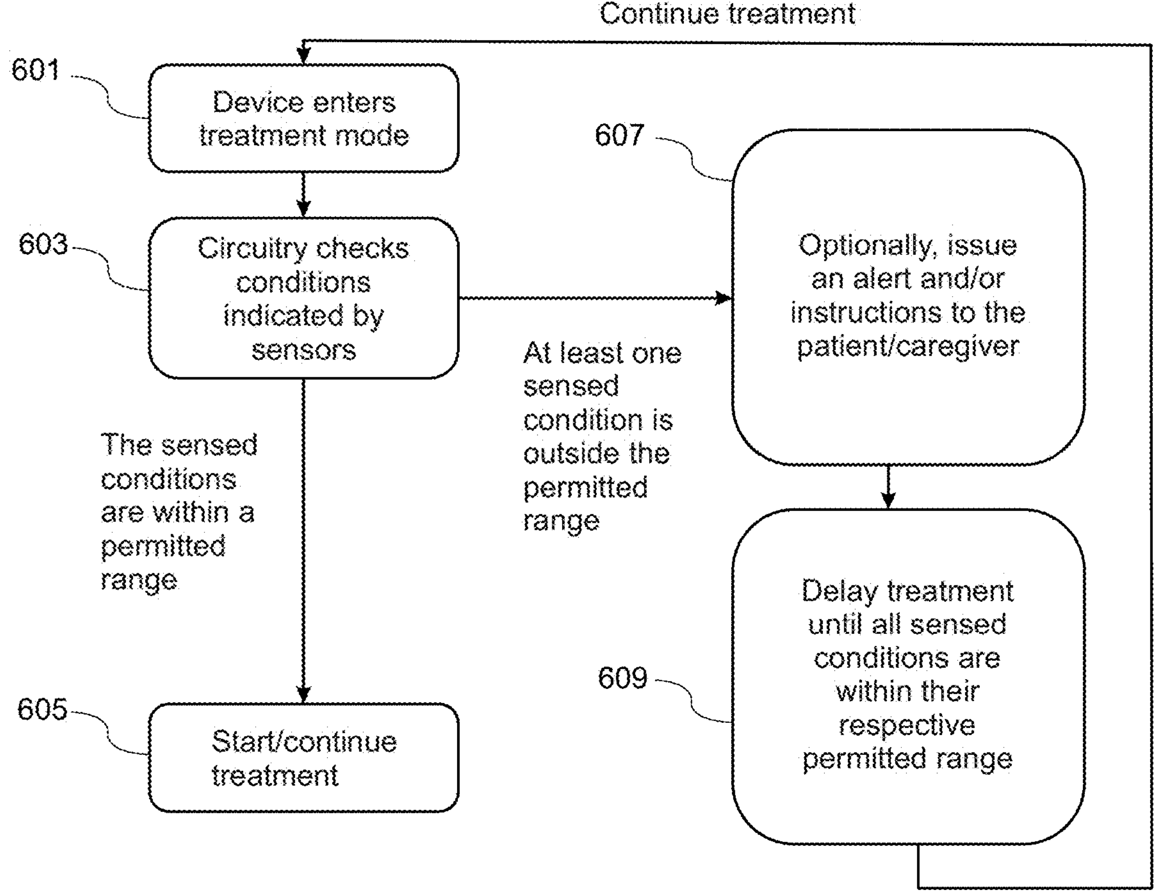
FIG. 6 shows an exemplary feedback loop of the control system, in which the circuitry checks sensed conditions, according to embodiments of the presently disclosed subject matter.

FIG. 6 shows an exemplary feedback loop of the control system, in which the circuitry checks sensed conditions, according to embodiments of the presently disclosed subject matter.

At 601, the device enters a treatment mode in which the actuators are ready to be activated for adjusting the struts. The device may enter the treatment mode automatically, e.g. based on the schedule defined by the treatment plan, and/or manually. In some embodiments, instructions for entering treatment mode are communicated to the circuitry from an external device, such as from the physician's computer, the user's cell phone app, or others.

At 603, the circuitry checks one or more conditions such as temperature, a weight or load acting on the device, acceleration, humidity, pressure and/or other conditions, based on indications received from one or more sensors. At 605, if the sensed conditions are within a permitted range, treatment (i.e. adjustment of the struts) is initiated or continued. At 607, if at least one sensed condition is outside its permitted range, the circuitry optionally issues an alert and/or instructions to the patient or caregiver, for example via an external device and/or via an interface (e.g. a screen) of the control unit itself. At 609, treatment is delayed until all sensed conditions are within their respective permitted ranges.

In some specific cases, if a sensed condition is out of the permitted range, an override may be allowed, and the treatment can be carried out. Such override can be performed for only some of the conditions, for example, an out-of-range temperature can be overridden, but an excess load cannot. In some embodiments, overriding an out-of-range condition can take place only if a physician and/or the patient confirmed that the treatment can be performed taking into account the out-of-range condition.

Generally, conditions that are outside their permitted range may have clinical effects on the patient and/or operational effects on the device. For example:

- With respect to temperature: if the ambient temperature is too low, tissues (e.g. muscles, tendons) may be stiffer and harder to stretch, potentially resulting in increased force being required for adjusting the struts. In such situation, strut adjustment may cause pain to the patient. If the ambient temperature is too high, operation of the actuators may be affected, and it would be desired to prevent overheating. Generally, when the ambient temperature sensed by the device is out of range, treatment can be delayed and the patient/caregiver may be instructed to move into a warmer environment or a cooler environment.
- With respect to load/weight: if an excess load is detected, this may imply a physical obstruction or other burden weighing down on the device, potentially interfering with strut adjustment. In some embodiments, excess load can be detected by measuring the current consumption of the actuators, which rises in correlation with the force generated by the actuators (the force is expected to increase with a higher load). When the current consumption of one or more actuators exceeds a certain limit, an excess load/weight alert may be issued, and strut adjustment may be delayed.
- With respect to acceleration: if a high acceleration is measured by the device, this can imply that the patient is currently moving at a fast pace. In such situation, it may be preferred to wait until the patient is rested and relatively still, before carrying out the strut adjustment. Optionally, the patient is instructed to stand still, sit, or otherwise stop moving.

In some embodiments, when treatment is delayed, the circuitry samples the sensors (all sensors or at least those that indicated out of range conditions) at constant time intervals, for example every 5 seconds, 10 seconds, 1 minute, 5 minutes, or intermediate, longer or shorter time intervals. Optionally, the sensors are sampled during the treatment itself (i.e. during a strut adjustment session), to verify that all conditions are still within their predefined ranges.

In some embodiments, in a case of delay, the circuitry is configured to compensate for the delay, for example by changing the actuation plan or suggesting a change therein. In some cases, the circuitry notifies the physician and/or caregiver and/or patient regarding the change.

The following FIGS. 7-10 relate to pressure measurements which can be carried out by the control unit of the bone fixation device. In general, the device control unit can be provided in one of two configurations: an hermetically sealed control unit, in which the housing of the control unit prevents entry of any external elements; and a selectively permeable control unit, in which the housing of the control unit is, for example, permeable to gas (e.g. air) but impermeable to liquids (e.g. water). In some embodiments, the housings of the actuators are constructed in a similar manner to the control unit, in one of the two configurations.

Figure 7A:
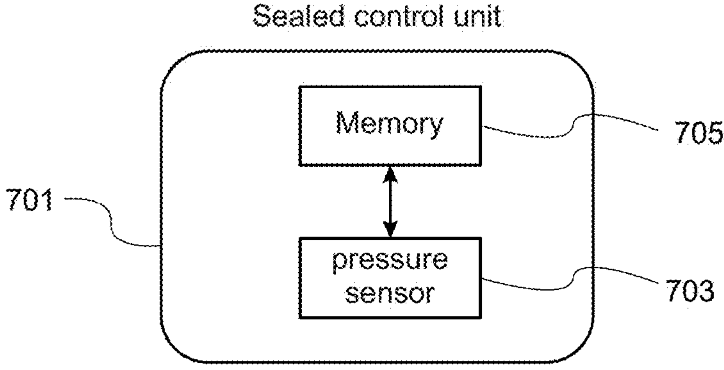
FIGS. 7A-B are a schematic diagram and an exemplary feedback loop of a sealed control unit of the bone fixation device, according to embodiments of the presently disclosed subject matter.
Figure 7B:
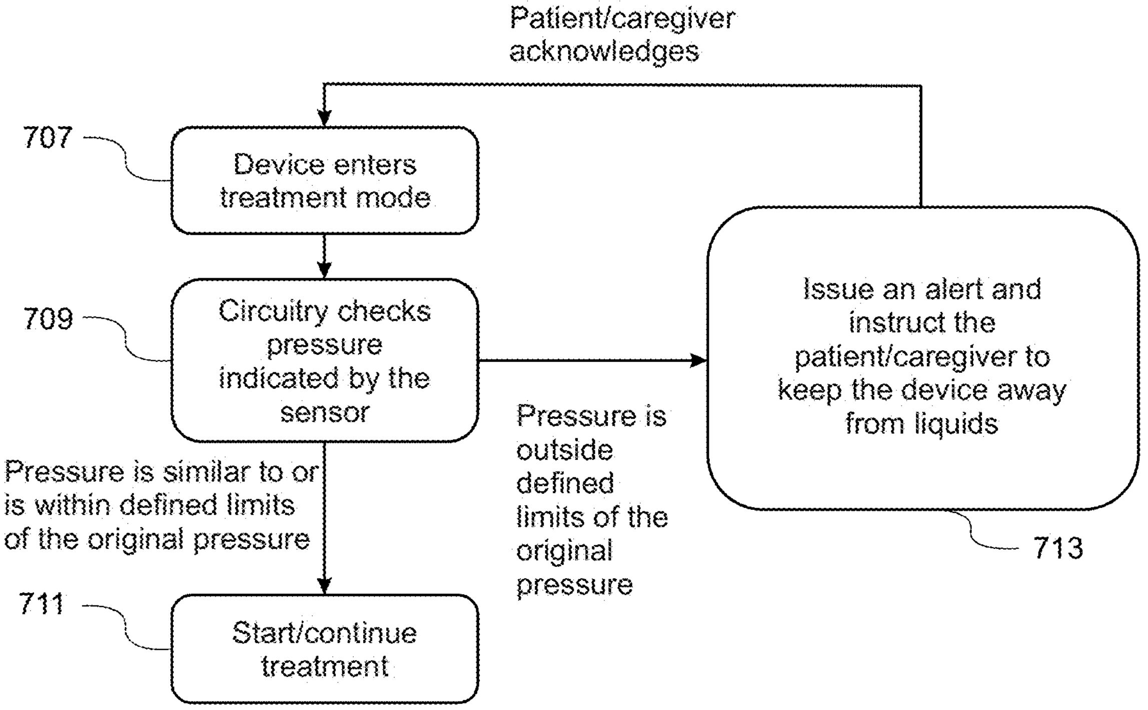

FIGS. 7A-B are a schematic diagram and an exemplary feedback loop of a sealed control unit of the bone fixation device, according to embodiments of the presently disclosed subject matter.

In FIG. 7A, housing 701 of the control unit provides a sealed enclosure, which prevents any external elements from entering the control unit. In some examples, the housing is constructed of a lightweight, durable material, e.g. medical grade plastics, polymers, composite materials, metals, or other suitable materials.

In some embodiments, one or more pressure sensors 703 inside the control unit are configured to measure the pressure, and the measured values can be saved in a memory 705. Since the sealed control unit prevents entry of liquids (which may be harmful to the electronic components of the control unit), the control unit can come in contact with water, enabling the patient to take showers, swim, and the like, while the bone fixation device is connected to their body.

In some embodiments, an original pressure which is measured, for example, during device assembly, is saved in the memory. As the control unit is sealed, the original pressure is expected to remain constant (or at least within close limits of the original pressure-which thereby define a permitted pressure range) at all times. In some cases, during manufacturing, sealing of the housing is verified by placing the control unit in a pressure chamber in which the pressure is either higher or lower than the original pressure, and checking whether the pressure measurement changed. If the pressure changed, then presumably there is a sealing defect, and the sealing is fixed.

Figure 8:
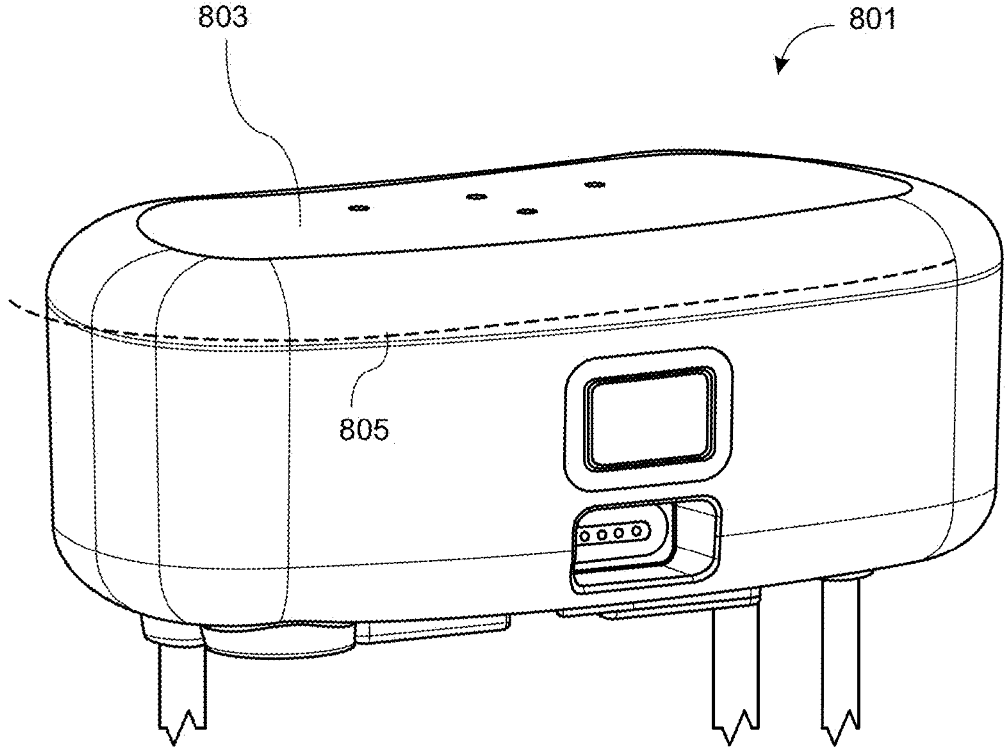
FIG. 8 is an example of a sealed control unit, according to embodiments of the presently disclosed subject matter.

In the exemplary feedback loop of FIG. 7B, at 707, the device enters treatment mode. At 709, the circuitry checks the pressure indicated by the pressure sensor. If the pressure (sensed inside the control unit) is similar to or within close limits of the original pressure (saved in the memory), then at 711 treatment is started or continued. If the pressure is outside the defined close limits of the original pressure, then at 713 the circuitry issues an alert that the sealing may have been breached, and instructs the patient (or caregiver) to keep the device away from liquids. Once the patient acknowledges this warning, in some embodiments, treatment may be continued, assuming that the patient remains in a dry environment, preventing any contact of the device with liquids; in other embodiments, it may be decided not to allow treatment until the sealing defect is fixed. FIG. 8 is an example of a sealed control unit, according to embodiments of the presently disclosed subject matter. The control unit 801 comprises a housing 803 which encapsulates the control circuitry of the device. A non-permeable adhesive 805 or gasketing may be used for ensuring the sealing is maintained at interfaces between different parts of the housing, (if such exist).

Figure 9A:
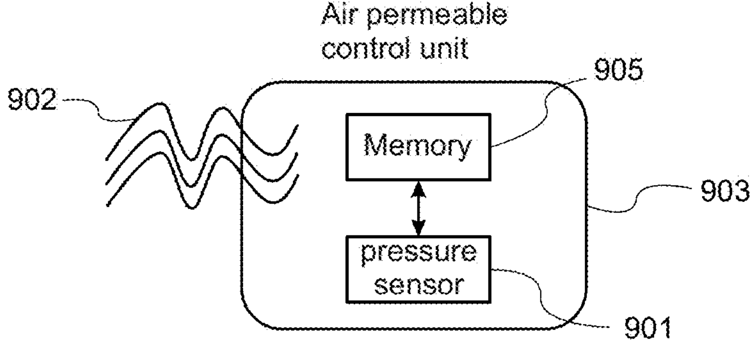
FIGS. 9A-B are a schematic diagram and an exemplary feedback loop of a selectively permeable control unit of the bone fixation device, according to embodiments of the presently disclosed subject matter.
Figure 9B:
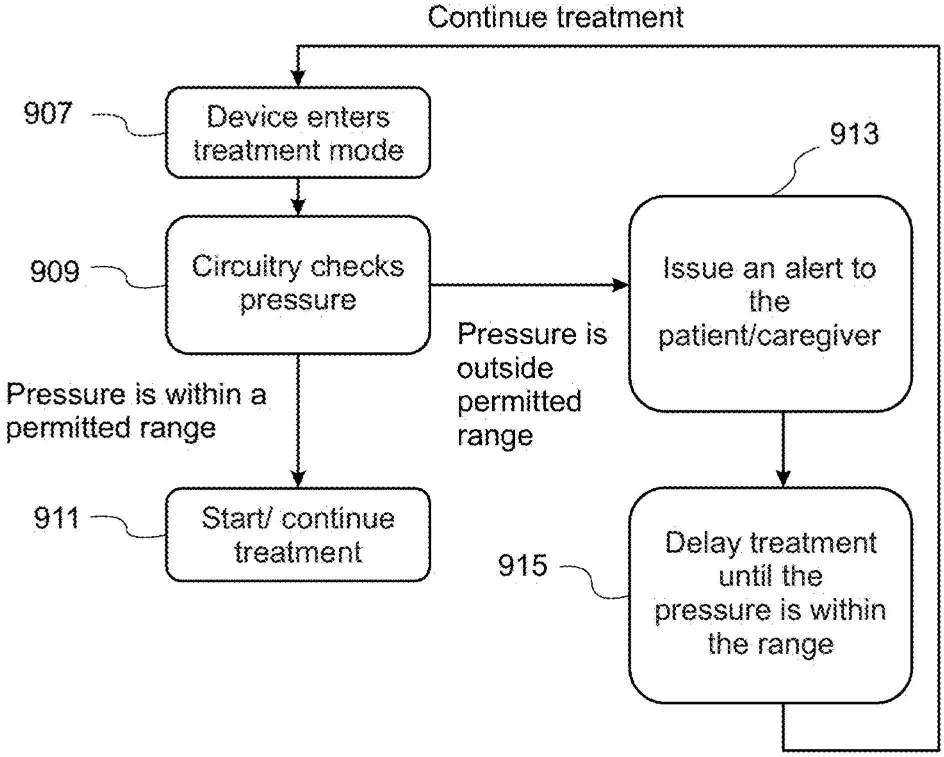

FIGS. 9A-B are a schematic diagram and an exemplary feedback loop of a selectively permeable control unit of the bone fixation device, according to embodiments of the presently disclosed subject matter.

In FIG. 9A, housing 901 of the control unit provides a selectively permeable enclosure, which allows, for example, gas (e.g. air 902) to freely exit and enter the control unit, but prevents entry of liquids, e.g. water, from entering the control unit. In some examples, the housing is constructed of an air permeable and waterproof material, e.g. ePTFE material such as GORE-TEX. In other examples, the material from which the housing is constructed is non-permeable, but comprises one or more openings which enable to passage of air but not of water, for example with the aid of a valve.

One or more pressure sensors 903 inside the control unit are configured to measure the pressure, and the measured values can be saved in a memory 905. Since the housing is air-permeable, pressure values measured inside the control unit are expected to match those of the environment. In the exemplary feedback loop of FIG. 9B, at 907, the device enters treatment mode. At 909, the circuitry checks the pressure indicated by the pressure sensor. If the pressure (sensed inside the control unit) is within a permitted range, then at 911 treatment is started (or continued). If the pressure is outside the predefined range (for example: the patient is on an airplane, experiencing low pressure conditions; the patient is underwater, experiencing high pressure conditions), then at 913 the circuitry issues an alert that the pressure is outside the permitted range; and at 915, treatment is delayed until the sensed pressure is within the permitted range. Checking the pressure and delaying the treatment accordingly may be advantageous because high or low pressure conditions may have clinical effects on the tissue or on the general physical condition of the patient, in which case it can be preferred to wait until the patient is within a normal pressure environment (for example, wait until the plane has landed, and only then begin adjusting the struts).

Figure 10A:
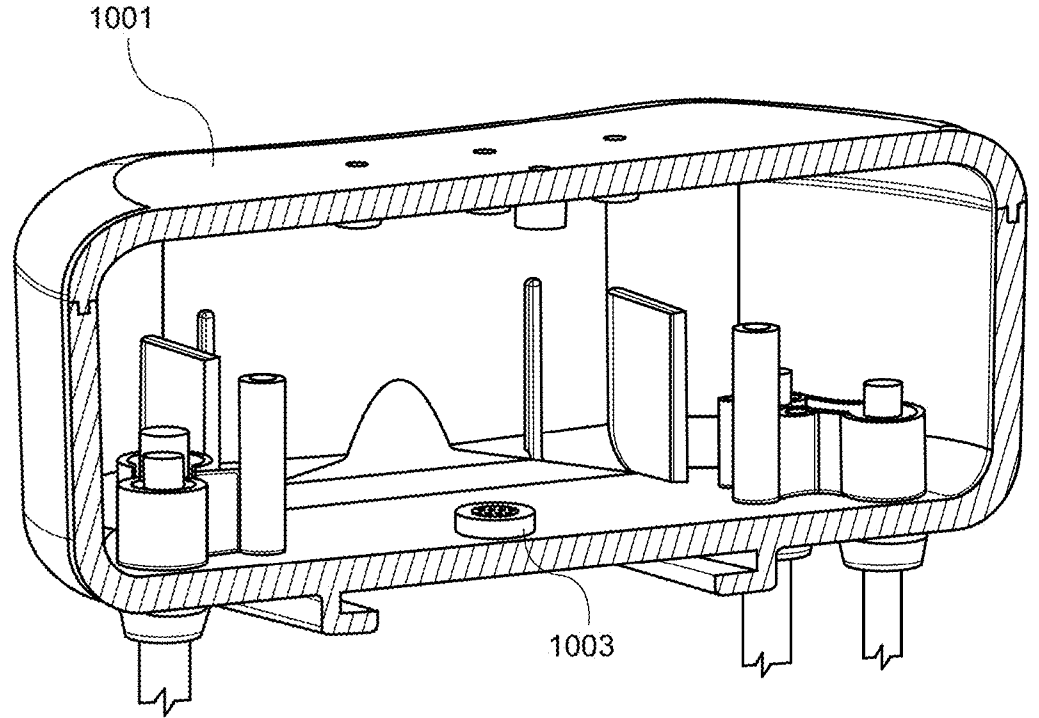
FIGS. 10A-B are schematic cross section views of a control unit which is ventilated, yet prevents the entry of liquids, according to embodiments of the presently disclosed subject matter.
Figure 10B:
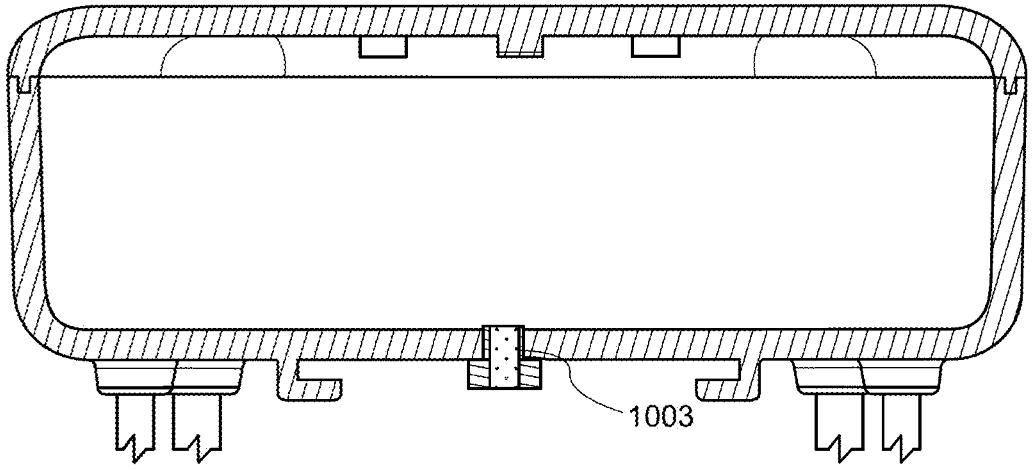

FIGS. 10A-B are schematic cross section views of a control unit which is ventilated, allowing air to freely enter and exit, yet preventing the passage of liquids. In this example, housing 1001 is sealed, and comprises a valve 1003 extending between an outside surface of the housing and an inside surface of the housing. Valve 1003 is configured to allow air flow through and prevent flow of water.

What is claimed is:

1. A control system for use with an adjustable bone fixation device having a frame connectible to bone tissue and a plurality of struts connected to the frame, the control system comprising:

- a plurality of actuators associated with the plurality of struts, each actuator configured for adjusting a length of at least one strut; and
- circuitry configured to:
  - signal the plurality of actuators to adjust the struts according to a predefined actuation plan which sets operational parameters and permitted ranges thereof;

determine a situation of potential failure associated with at least one actuator and involving at least one of said operational parameters being out of the permitted range;

delay, based on the determined situation of potential failure, entering an error mode in which the plurality of actuators are stopped; and re-attempting, after waiting a preset time period, adjustment of one or more of the struts according to the predefined actuation plan.

2. The control system according to claim 1, wherein the predefined actuation plan sets permitted ranges for one or more of the following operational parameters or indicators thereof:

A. timing of adjustment;

B. an adjustment duration;

C. torque to be applied by the actuator onto the one or more struts; or

D. a desired adjustment in the length of the one or more struts.

3. The control system according to claim 1, wherein the circuitry is configured to select a recovery protocol from a plurality of recovery protocols stored in a memory of said control system.

4. The control system according to claim 3, wherein the plurality of recovery protocols include one or more of the following protocols or a combination thereof:

(protocol a) the re-attempted, after waiting a preset time period, adjustment of the one or more struts;

(protocol b) moving the strut in a reciprocating motion along a predefined distance; or (protocol c) re-attempting the adjustment that was not carried out or was only partially carried out in one or more successive actuation sessions.

5. The control system according to claim 4, wherein the circuitry comprises one or more sensors configured for sensing conditions that are associated with one or both of the adjustable bone fixation device and its surroundings, the one or more sensors including: a temperature sensor; a humidity sensor; a sensor configured for detecting a current posture of a patient; a sensor configured for detecting a current orientation of a body part to which the adjustable bone fixation device is connected; an acceleration sensor; a weight/load sensor; and wherein the circuitry is configured to check, upon entering a treatment mode, whether the conditions sensed by the one or more sensors are within a permitted range.

6. The control system according to claim 5, wherein the plurality of recovery protocols further include (protocol d): delaying adjustment of the one or more struts and re-attempting it when at least one of:

(a) the one or more sensors detect a desired change in at least one of the conditions; or (b) the conditions sensed by all of said one or more sensors are within a permitted range.

7. The control system according to claim 4, wherein the circuitry is configured to implement more than one recovery protocol, and to stop when either adjustment of the strut is completed or a predefined time period passed.

8. The control system according to claim 1, wherein the control system comprises one or more sensors configured for measuring said operational parameters or indicators thereof.

9. The control system according to claim 1, wherein the circuitry is configured to identify whether the potential failure is associated with a single actuator or is associated with multiple actuators.

10. The control system according to claim 9, wherein if the potential failure is associated with a single actuator, the circuitry controls operation of the plurality of actuators according to one or more of the following:

(A) continue operation of all actuators except for the actuator for which potential failure had been indicated;

(B) carry out a recovery protocol for the actuator for which potential failure had been indicated, and only then continue operation of all actuators; or (C) stop operation of all actuators.

11. The control system according to claim 1, wherein the circuitry is configured to one or both of suggest and effect changes in the predefined actuation plan for compensating for a recovery protocol which involves a delay in strut adjustment.

12. An adjustable bone fixation device, comprising:

a frame connectible at least indirectly to bone tissue and comprising at least two spaced apart portions;

a plurality of struts extending between the at least two spaced apart portions of the frame; and the control system according to claim 1, whereby the plurality of actuators are operably connected to the plurality of struts.

* * * * *